United States Patent [19]

Ryan

[11] 4,257,425

[45] Mar. 24, 1981

[54] BIOPSY SPECIMEN COLLECTOR

[75] Inventor: James P. Ryan, Weymouth, Mass.

[73] Assignee: Codman & Shurtleff, Inc., Randolph, Mass.

[21] Appl. No.: 45,034

[22] Filed: Jun. 4, 1979

[51] Int. Cl.³ .............................................. A61B 10/00
[52] U.S. Cl. ................................... 128/758; 128/278; 128/304
[58] Field of Search .............. 128/752, 757, 758, 749, 128/304, 302, 276–278, 201.21

[56] References Cited

U.S. PATENT DOCUMENTS

| | | | |
|---|---|---|---|
| 1,487,252 | 3/1924 | Lore | 128/276 |
| 2,242,108 | 5/1941 | Bullowa et al. | 128/201.21 |
| 3,066,672 | 12/1962 | Crosby et al. | 128/276 |
| 3,308,825 | 3/1967 | Cruse | 128/276 |
| 3,318,307 | 5/1967 | Nicastro | 128/201.21 |
| 3,661,144 | 5/1972 | Jensen | 128/758 |
| 3,774,612 | 11/1973 | Marco | 128/304 |
| 3,774,613 | 11/1973 | Woods et al. | 128/304 |
| 3,828,781 | 8/1974 | Rothman | 128/278 |
| 3,889,657 | 6/1975 | Baumgarten | 128/304 |
| 4,141,360 | 2/1979 | Lasswell | 128/276 |

FOREIGN PATENT DOCUMENTS

| | | | |
|---|---|---|---|
| 2805285 | 8/1978 | Fed. Rep. of Germany | 128/276 |
| 1718 | 5/1979 | European Pat. Off. | 128/758 |

*Primary Examiner*—Kyle L. Howell
*Attorney, Agent, or Firm*—Donal B. Tobin

[57] ABSTRACT

A biopsy specimen collector for use with a vacuum source includes a closed receptacle having an inlet opening and an outlet opening. The outlet opening is adapted to be connected to the vacuum source. A removable cover provides access into the interior of the receptacle. A fluid channel tube inside the receptacle has one end connected to the outlet opening, with its other end being open and being positioned substantially at the geometric centroid of the receptacle to facilitate operation of the collector without regard of its orientation during use.

6 Claims, 5 Drawing Figures

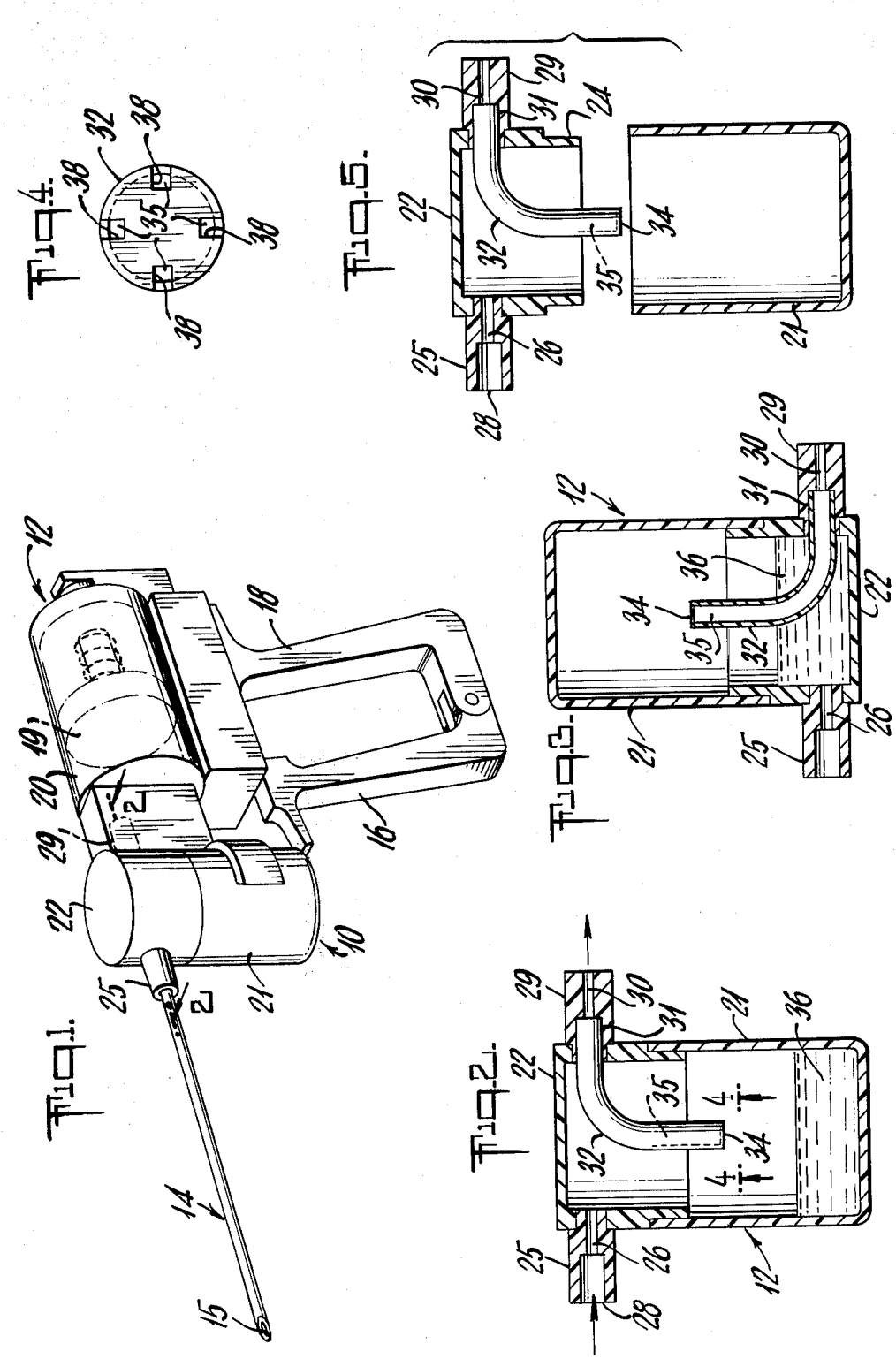

4,257,425

BIOPSY SPECIMEN COLLECTOR

BACKGROUND OF THE INVENTION

The present invention relates to a biopsy specimen collector, and, more particularly concerns such a collector for use with a vacuum source and an endometrial curette in performing uterine biopsies.

Biopsy procedures, particularly of the uterus, are performed with the use of an elongate curette usually attached to a vacuum source. The physician generally inserts the curette into the body cavity to be sampled and relies upon scraping cutting action at the tip of the curette to dislodge a specimen from the walls of a cavity. Then, with the properly applied suction from the vacuum source, the specimen may either be collected from the tip of the curette or, in some instances, the specimen may travel along the length of the curette whereupon it may be collected at the curette's proximal end. One such biopsy specimen instrument is described in U.S. Pat. No. 3,561,429.

In relying upon suction from a vacuum source to facilitate the collection of such a specimen, body liquids often present a problem in such a procedure. For instance, in addition to any tissue which may be dislodged from the cavity wall, blood and other body liquids are drawn into the open end of the curette. If these liquids travel along the curette and ultimately into the vacuum source, problems with the operation of the vacuum source could arise. Particularly, if the vacuum source is a hand-held vacuum pump, blood flow into the piston chamber which produces the vacuum could not only clog its motion, but possible leak out of the device. Even if a collection jar or vial were to be used with merely an inlet port and an outlet port, there would be a danger of blood or other liquids passing into the vacuum line, since any liquid collected in the jar could be shaken sufficiently so that it would enter the outlet opening of the jar and thus travel into the vacuum line. It is appreciated that this liquid shaking or moving would occur since the physican often includes side to side rocking of the pump and curette in order to properly scrape the cavity wall; thus, any liquid which enters the collection jar would be susceptible to this rocking movement with the potential that the liquid may enter the vacuum line and thus cause problems. Thus, the present invention is directed to the solution of these problems.

SUMMARY OF THE INVENTION

A biopsy specimen collector for use with a vacuum source comprises a closed receptacle having an inlet opening and an outlet opening. The outlet opening is adapted to be connected to a vacuum source. Means for access into the interior receptacle is provided. Fluid channel means inside the receptacle has one end connected to the outlet opening with its other end being open and positioned substantially at the geometric centroid of the receptacle. This facilitates operation of the collector without regard for its orientation during use.

From the structural standpoint, the biopsy specimen collector of the present invention is notably different from a simple collection jar in a number of respects. For instance, the present collector includes a substantially centroidally located opening which leads to the vacuum source. As long as the receptacle which receives the specimen and any body liquids always remains less than half full, the physician may orient the collection curette and the collector receptacle in any direction while avoiding the undesirable passage of liquid into the vacuum source line. Inasmuch as most biopsies can be performed with the collection of minimal amounts of body liquids along with the intended tissue to be scraped, the half-full limitation as previously described in using the present invention should not present any problems. In other words, most biopsy procedures can be completed without drawing so much body liquid into the receptacle that it would more than half fill the receptacle. Accordingly, the centroidally located opening connected to the vacuum source not only prevents undesirable liquids from entering the vacuum line but advantageously allows the physician to rock and move the biopsy instrument in any degree necessary for the procedure to be satisfactorily completed.

BRIEF DESCRIPTION OF THE DRAWINGS

FIG. 1 is a perspective view of the preferred biopsy specimen collector attached to a hand-held vacuum pump with an endometrial curette connected to the collector;

FIG. 2 is a cross-sectional view taken along line 2—2 of FIG. 1;

FIG. 3 is a cross-sectional view similar to FIG. 1, but with the collector shown in an inverted position as it may be oriented during use;

FIG. 4 is an enlarged end view of the centroidally located open end of the vacuum tube taken along line 4—4 of FIG. 2; and FIG. 5 is an exploded view of the preferred collector with the cover removed for access to the interior of the receptacle.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Referring to the drawings, particularly to FIG. 1, there is illustrated the preferred biopsy collector 10, in this instance, attached to a hand-held vacuum pump 12 by means of a snap fit into resilient brackets on the pump. Extending from collector 10 is an endometrial curette 14. This curette is generally a hollow, elongate slender tube with an opening 15 at its distal end for both scraping and receiving a specimen from the body cavity being probed. It is appreciated that vacuum pump 12 is adapted to produce a suction force through collector 10, which is also transmitted through curette 14 for drawing in the specimen through opening 15. The squeezing action of pump handles 16 and 18 causes piston 19 to move inside cylinder 20, to in turn produce a vacuum within the cylinder which communicates with the connected biopsy connector. It is understood, that, while the general operation of hand-held pump 12 is briefly outlined here, any suitable vacuum source can be used with collector 10 to satisfy the purposes of this invention.

Referring to FIGS. 2-5, the specific details of the preferred biopsy specimen collector are illustrated. The collector consists generally of two parts, a receptacle 21 and a removable cover 22. Receptacle 21 is in the form of an open ended cylindrical cup. Cover 22 is adapted to fit into or over the open end of receptacle 21 to provide a closure therefore. This fit between cover 22 and receptacle 21 may be a snap-fit, press-fit or screw-thread fit, all of which should preferably have a sufficiently tight seal to facilitate the vacuum drawing conditions inside the collector. Cover 22 is also preferably an open-ended cylindrical cup with a shoulder step 24 around its periphery spaced a short distance inwardly from its open end. This shoulder provides the mating ability between cover 22 and receptacle 21 to contribute to the proper fit of these two components. However, cover 21 is also readily removable in order to provide access into the interior of receptacle 21. Near the top surface of cover 22, two fluid ports are provided, in this instance, being diametrically opposed to each other. Inlet port 25 is a short cylindrically shaped extension from the periphery of cover 22, and includes a passageway 26 therethrough in fluid communication with the interior of the closed collector. A counter bore 28 is sized to receive the outside diameter of the endometrial curette in a snug fit during use. Outlet port 29 is similar to inlet port 25 with a passageway 30 extending therethrough and is adapted to be connected to a vacuum source by an appropriate connection. A counter bore 31 is provided in the interior section of the outlet port. This counter bore is adapted to receive a hollow tube 32, which extends from outlet port 29 into the interior of cover 22. Tube 32 includes an open end 34 providing fluid access through the lumen 35 of the tube and passageway 30 in the outlet port. When cover 22 is placed on receptacle 21 the interior boundaries of this closed structure (except for the inlet and outlet openings) define a certain geometric configuration. Hollow tube 32 is arranged so that its open end 34 is positioned substantially at the geometric centroid of the collector defined by such interior boundaries.

In operation, the substantially centroidally located opening 34 communicating with outlet port 29 facilitates use of the collector without regard for its orientation. For example, as seen in FIG. 2, when vacuum is applied the airflow travels from inlet port 25 into the collector and out the outlet port such as indicated by the arrows. If, in addition to scraped tissue which is desirably drawn into the collector, undesirable quantities of blood 36 or other body liquids is drawn into the collector, it will settle at the bottom of receptacle 21 in the orientation illustrated in FIG. 2. On the other hand, and as alluded to above, the operator often relies upon side to side turning of the endometrial curette in order to properly collect the specimen. With the structure of the present invention, even an inverted orientation of the collector, as illustrated in FIG. 3, will not disturb its operation. In this case, blood 36 will lie within the bottom confines of cover 22. Thus, the ability of body fluids entering opening 34 and travelling into the vacuum source through outlet port 29 is rather remote. Since liquid in the vacuum source can disturb its proper operation, it can be appreciated that such a preventative measure is highly advantageous. The centroidally located opening 34 will provide this preventative measure. While it may be noted in FIG. 3 that blood 36 or other body liquids may escape through inlet port 25, this is generally not a problem inasmuch as this type of inverted orientation would only be brief and encountered during operation of the vacuum source so that the flow of fluid would be an inward direction into the collector.

Although various configurations for opening 34 at the end of hollow tube 32 may be fabricated, one such configuration is illustrated in FIG. 4. Rather than have one general opening communicating with lumen 35, four apertures 38 are provided. Each aperture 38 is thus reduced in cross-section from the normal cross-section of lumen 35. As a result of this opening reduction, this end of the hollow tube serves as a strainer to prevent the specimen tissue from entering the hollow tube. Other strainers or filters may be included to assure proper air flow through the tube but to eliminate or reduce any possibility of tissue entering the tube.

While in no way limiting the construction of the specimen collector of the present invention, the preferable material of the cover and receptacle is plastic, such as polypropylene; the collector is sized to receive approximately 1.2 ozs. (36.5 cc) up to its geometric centroid.

Thus, there has been provided in accordance with this invention a biopsy specimen collector which eliminates or reduces any inadvertent flow of blood or body liquids into the vacuum source, while assuring the operation of the collection procedure in any orientation of the collector assumed by the operator.

1. A biopsy specimen collector capable of use in any orientation and adapted for use with a vacuum source comprising:
    a receptacle including a cover portion having a transverse wall and a sidewall projecting from and extending about the periphery of said transverse wall and having an open end;
    the edge of the sidewall surrounding the open end of the cover portion having a recess for receiving a collection portion;
    said sidewall further including an inlet opening and an outlet opening therethrough;
    an inlet tube disposed in said inlet opening and having a first bore extending from its distal end part way through said inlet tube and having a second bore extending from said first bore through said inlet tube to the inside of said cover portion;
    an outlet tube disposed in said outlet opening and having a first bore extending from its distal end part way through said outlet tube and having a second bore extending from said first bore through said outlet tube into the interior of said cover portion;
    a curved tube having a first end disposed in said second bore of said outlet tube and having a second end extending in a direction away from said transverse wall of said cover portion;
    said receptacle including a collection portion having a transverse wall and a sidewall projecting from and extending about the periphery of said collection portion transverse wall and having an open end;
    the periphery of said collection portion sidewall adapted to mate with the recess on the edge of the cover portion sidewall so that the cover portion and collection portion are tightly engaged together to form a receptacle wherein the interior boundaries of said receptacle define a geometric configuration, the open end of said curved tube being located substantially at said geometric centroid.

2. The specimen collector of claim 1 further including a curette frictionally disposed in said first bore of said inlet tube.

3. The specimen collector of claim 1 further including a strainer affixed over the open end of said curved tube which prevents specimens from entering said curved tube when said specimen collector is inverted.

4. The specimen collector of claim 1 wherein the diameter of said inlet tube second bore is less than that of said first bore.

5. The specimen collector of claim 1 wherein the diameter of said outlet tube second bore is greater than that of said first bore.

6. The specimen collector of claim 1 wherein said inlet tube, said outlet tube and said cover portion are formed as a unitary element.

* * * * *